United States Patent [19]

Lau et al.

[11] Patent Number: 4,661,408

[45] Date of Patent: Apr. 28, 1987

[54] COATED CHROMIUM DIOXIDE PARTICLES

[75] Inventors: Hon-Peng P. Lau, Newark; Esther K. Yang; Howard W. Jacobson, both of Wilmington, all of Del.

[73] Assignee: E.I. Du Pont de Nemours and Company, Wilmington, Del.

[21] Appl. No.: 841,107

[22] Filed: Mar. 18, 1986

[51] Int. Cl.$^4$ ................................................. B32B 5/16
[52] U.S. Cl. .................................... 428/405; 530/413; 428/302
[58] Field of Search ................ 530/413; 428/402, 403, 428/405, 302

[56] References Cited

U.S. PATENT DOCUMENTS

| | | | |
|---|---|---|---|
| 3,437,502 | 4/1969 | Werner | 106/300 |
| 3,512,930 | 5/1970 | Bottjer et al. | 23/145 |
| 4,068,038 | 1/1978 | Montiglio et al. | 428/404 |
| 4,141,687 | 2/1979 | Forrest et al. | 23/230 |
| 4,275,114 | 6/1981 | Schoenafinger et al. | 428/328 |
| 4,297,337 | 10/1981 | Mansfield et al. | 424/1 |

*Primary Examiner*—Edith Buffalow

[57] ABSTRACT

Chromium dioxide has favorable magnetic properties which make it desirable as a solid support in heterogeneous immunoassays. However, to be useful in such assays it must be protected against hydrolytic degradation. This invention provides magnetic particles useful in immunoassays having a core of $CrO_2$ which has a reduced surface, the core coated with silica and further coated with a silane.

18 Claims, No Drawings

COATED CHROMIUM DIOXIDE PARTICLES

BACKGROUND OF THE INVENTION

1. Field of the Invention

This invention relates to surface modification of ferromagnetic chromium dioxide particles. The modified particles are useful in heterogeneous diagnostic assays and bioaffinity separations.

2. Background Art

The concept of using magnetically responsive particles to effect separations of bioactive materials is old in the art (Hedin, C. G., Biotech. Bioeng. Symp. No. 3 (1972) 173-174; Robinson, P. J., et al, Biotech. Bioeng. (1973) 15, 603-606). The concept has been extended over time to include affinity purification of enzymes, proteins or microorganisms applicable to any sorption-desorption process (Dunhill, P., et al, Biotech. Bioeng. (1974) 10, 987-990; Horisberger, M., Biotech. Bioeng. (1976) 18, 1647-1651).

Hersh, L. H., et al describe in U.S. Pat. No. 3,933,997 the first use of magnetically responsive particles as the solid support in heterogeneous immunoassays. The preferred particle described is a ferrous oxide particle; however, CoO, NiO, $Mn_2O_3$, CoMnP particles are also disclosed and claimed.

Subsequently, many varieties of magnetically responsive particles have been described. Ithakissios in U.S. Pat. No. 4,115,534 discloses the use of composite microparticles employing a permeable, solid, water-insoluble matrix comprising a proteinaceous material, a polysaccharide, a polyurethane or mixtures thereof. A variety of ferromagnetic substancess may be employed, $BaFe_{12}O_{19}$, $Fe_3O_4$, CoO, NiO, $Mn_2O_3$, CoMnP, iron or nickel, according to this invention.

Forrest et al in U.S. Pat. No. 4,141,687 describe and claim the use of composite microparticles which have a specific gravity near that of the reaction millieu. This improvement allows the particles to remain suspended in the solution allowing for more efficient capture kinetics. Again, a variety of ferromagnetic substances are described and claimed as part of this invention. This list includes $CrO_2$ along with iron, magnetic iron oxides, nickel or cobalt. However, the density of $CrO_2$ particles, 4.85, would limit the number of particles which could be incorporated into the composite matrix. Microparticles thus prepared would be magnetically very dilute, requiring high gradient field strengths for separation.

A still further improved magnetically responsive particle is described by Mansfield et al in U.S. Pat. No. 4,197,337. These particles are porous glass microparticles with magnetic material imbedded within them. This gives the particles the properties of high surface area, inertness and being substantially superparamagnetic. This high surface area again favors rapid reaction kinetics and increases capacity of the individual particles. Being substantially superparamagnetic basically means the particles do not retain much magnetic memory, or rentitivity, when removed from a magnetic field. This means that particles can be repeatedly separated in a magnetic field without affecting the ability to redisperse those particles. This is of advantage in sandwich immunoassays where multiple washing steps may require repeated separation and redispersion. These particles are of necessity magnetically dilute and thus also require relatively high field strengths for separation.

Perhaps the most recent improved magnetic particle is that described by Chagnon et al in Danish Application DK No. 2374/84 and commercially available under the trade name Biomag ® from Advanced Magnetics. These particles are composed of a cluster of microcrystals bound together by a silane coating. These particles have a diameter in the range 0.1 to 1.5 $\mu M$ with a very high surface area, 100-150 $m^2/g$, a settling time of greater than 1.5 hours and a magnetic separation time of less than 10 minutes. The long settling time of the particles favors rapid reaction kinetics. The microcrystal size of Biomag ® is also substantially smaller than those described by Mansfield; thus, the particles are truly superparamagnetic which eliminates the problem of magnetic aggregation. The metal oxide is defined as a group of crystals consisting of transition metal oxide with "ferro-spinel" structure which excludes rutile structure $CrO_2$. Indeed, the teaching of DK No. 2374/84 would not be applicable to $CrO_2$ particles because it would not adequately protect the $CrO_2$ from hydrolysis. This invention provides particles which take advantage of the favorable magnetic properties of $CrO_2$ in a composition in which the $CrO_2$ is protected from hydrolysis.

The protected $CrO_2$ particles of this invention have the following properties:

low remanent magnetism and favorable surface structure—allowing repeated magnetic separation/dispersion cycles;

rapid separation in a magnetic field;

high surface area for high capture capacity;

a highly stable particle for maximum reagent shelf life.

It is known that $CrO_2$ is ferromagnetic and crystals or particles of $CrO_2$ are useful in the production of magnetic recording tapes. However, magnetic recording applications have requirements quite different from immunoassays, specifically, in a hydrolytic particle stability and particle size.

It is well known that the hydrolytic stability of $CrO_2$ crystals is poor even relative to the needs of magnetic tape where the crystals are bonded to a polymer (relatively) isolated from water. In U.S. Pat. No. 3,512,930, Bottjer and Ingersoll teach a reductive surface treatment of $CrO_2$ to improve its stability. In this process the surface of the $CrO_2$ crystal is reduced to form a protective layer which is much more hydrolytically stable. This coating, however, is easily reoxidized by air. The requirements for resistance to air oxidation are much greater for immunoassay applications than for tape applications so the particles while suitable for tape applications are not suitable for use as solid supports in immunoassays. Also of note is that the reduced surface of the crystal is nonmagnetic, thus a minimal coat is used in tape applications. As will be shown below a thick coating reducing the magnetic properties of the particle is advantageous in immunoassay applications.

Further means of stabilization of $CrO_2$ has been described such as that in U.S. Pat. No. 4,275,114 issued to Schoenafinger. This patent teaches the use of a block copolymer of siloxane units and alkyleneoxy units. Schoenafinger does not consider stability in aqueous solution as would be necessary for immunoassay use nor does he suggest that the particles described would be useful for such applications.

Another alternate approach to surface stabilization of $CrO_2$ particles is disclosed in U.S. Pat. No. 4,068,038 in which one or more insoluble or sparingly soluble cationic or anionic compounds such as Mg, Zn, Ce, La, Fe, Mn and Co with $MoO_4 (-2)$, $WO_4 (-2)$ or $PO_4 (-3)$, or hydrated or unhydrated oxides or hydroxides of amphoteric metals such as silicon, titanium or tin deposited on the surface. This means of stabilization has the advantage of retaining more of the high ferromagnetic properties desired for tape applications.

It is known that a dense silica coating improves the opacity and dispersibility of $TiO_2$ particles for use as a pigment, U.S. Pat. No. 3,427,507. It is also known that $CrO_2$ is isostructural with $TiO_2$. As described below encapsulating the surface reduced $CrO_2$ in silica provides significant advantages in immunoassay applications.

In order for any magnetic particle to be useful as a solid support in heterogeneous immunoassays, it must be derivatised. Since the original teachings of Hersh et al the use of functionalized silanes has been a preferred intermediate between the particle and the bioactive protein. Processes such as those described by Weetall, H. H. in U.S. Pat. No. 3,652,761 are illustrative of this procedure. The functionalized silanes can then be linked to bioactive reagents either directly, with homobifunctional or heterobifunctional crosslinkers.

Another useful characteristic for a magnetic particle to be used in immunoassay is a relatively high, but well controlled, particle size distribution. U.S. Pat. No. 4,524,008 issued June 18, 1985, to Chen describes an improved method for controlling $CrO_2$ particle size.

We have found that $CrO_2$ particles exceptionally well suited to use in immunoassays and other applications constituting bioaffinity separations can be produced using a multilayer coating process to stabilize and functionalize particles.

SUMMARY OF THE INVENTION

The magnetic particles of this invention are sufficiently hydrolytically stable to be useful as solid supports in heterogeneous immunoassays and bioaffinity separations. The core of the particles is acicular, rutile chromium dioxide. This material and its preparation are described in U.S. Pat. No. 4,524,008 and U.S. Pat. No. 3,512,930 which are incorporated by reference. The chromium dioxide particles have a surface area of 5-100 $m^2/g$, coercivity of 100-750 oersteds, remanent magnetization of 5-45 emu/g and saturation magnetization of 8-85 emu/g. These particles are surface stabilized as taught in U.S. Pat. No. 3,512,930. The stabilized surface layer is characterized by its X-ray diffraction pattern which exhibits a line corresponding to an interplanar spacing of 316.8 pm.

The chromium dioxide particles are further stabilized with a coating of $SiO_2$. The weight of $SiO_2$ coating the particles is greater than about 1% and preferably from 2-6% of the weight of the chromium dioxide.

The silica coated chromium dioxide is then further coated with a silane to both further stabilize the particle and to provide binding sites for proteins. The technique of attaching antibodies to inorganic supports using silanes is taught in U.S. Pat. No. 3,652,761 and U.S. Pat. No. 3,933,997. The choice of silane is dictated by the need to bind proteins to the magnetic particle, and a wide variety of such compounds are available.

The magnetic particle when coated with silica and silanized has a particle size of 0.5 to 5 $\mu m$ and a remanent magnetization of 8 to 21 emu.

DETAILED DESCRIPTION OF THE INVENTION

Magnetic characteristics desirable for biological applications are related to high saturation moment ($\sigma_s$), low coercivity (Hc) and low retentivity ($\sigma_r$), which requires particles to have high surface area and low aspect ratio (the ratio of cross section diameter to length). Accordingly, the particles have high specific surface areas, ranging from 5-100 $m^2/g$. Preferably, the particles have a surface area in the range of 30 to 80 $m^2/g$ and more preferably 40 to 70 $m^2/g$. Raw particles are commercially prepared according to U.S. Pat. No. 2,923,683 and upgraded by pulverizing and heating for 2 hours at 335° C. By upgrading is meant conversion of any oxides of chromium other than $CrO_2$, e.g., $Cr_2O_3$ or $Cr_3O_8$ to $CrO_2$.

The unstable surface of $CrO_2$ particles to chemical reduction and self disproportionation is protected by a controlled reduction treatment. This surface reduction treatment is taught in U.S. Pat. No. 3,512,930. This patent is directed to production of $CrO_2$ particles for magnetic recording uses. For producing particles sufficiently stable for immunoassay applications the same reducing procedure described in the patent may be used, but the stronger reducing agents and longer reaction times are preferred. Particularly preferred is the reduction of the $CrO_2$ particles using sodium bisulfite as follows.

Two hundred fifty grams of upgraded $CrO_2$ particles is milled with 100 g of sodium bisulfite in 1.75 L water for an hour at room temperature. The mixture is then aged for about a week in a closed storage container. This reductive surface treatment converts a large portion of each ferromagnetic core to the nonmagnetic $Cr^{+3}$ layer, which reduces magnetic interactions between particles and lowers retentivity to the extent that the particles become redispersible upon repeated exposure to magnetic field. The particles are dialyzed against water to remove the excess salt and stored as spray dried powder or used immediately. Magnetic separation is avoided throughout the process to minimize magnetic aggregation. Centrifugation or filtration is also avoided to prevent excessive irreversible agglomeration.

The protective layer on the $CrO_2$ particles produced by the surface reduction treatment can be characterized in several ways. As reported in U.S. Pat. No. 3,512,930 the protective surface layer can be characterized by an X-ray diffraction pattern corresponding to an interplanar spacing value of 3.151±0.006 Angstroms which corresponds to 315.1±0.6 pm. However, it is now known that this value is based on an incorrect assignment of the $CrO_2$ peak. The correct interplanar spacing is 316.8 pm. This value is believed to be correct, but it should be recognized that slight variations due to differences in X-ray diffraction equipment and interpretation of results will not remove the measured particles from the scope of this invention.

The effectiveness of the protective layer can also be determined by the rate at which chromate ions leach from the particles in a buffered aqueous solution. The chromate leaching test is performed as follows: Five mg of the $CrO_2$ particles are washed three times with 1 mL of 10 mM sodium phosphate buffer (pH7). Between washes, the particles are separated magnetically. The washed particles are suspended in 1 mL of phosphate buffer and heated at 80° C. for one hour. After magnetic separation the absorbance of the supernatant at 372 nm is measured on a spectrophotometer. Unprotected $CrO_2$ particles tested according to the above procedure give absorbances of >3. $CrO_2$ particles with a reduced surface give absorbances of <0.35.

The surface-reduced particles are not stable in aqueous suspension because the reduction process is readily reversed. To stabilize the core particles against reoxidation they are coated with an inorganic surface layer. This coating resists oxygen diffusion and provides reactive groups which form a site to link functional groups to the magnetic core. Examples of substances capable of forming said inorganic surface layer are silica, alumina and zirconium oxychloride, with silica being most preferred.

Silica is deposited on the $CrO_2$ according to the process set out in U.S. Pat. No. 3,437,507. In a preferred embodiment the $CrO_2$ is first conditioned with a small amount of alumina which provides better deposition on the silica. Still more preferred is the incorporation of a small amount of $B_2O_3$ in the $SiO_2$ layer. The weight ratio of alumina to $CrO_2$ in the solution used to coat the preferred particle is from 0.001–0.1, and the weight ratio of $B_2O_3$ to $SiO_2$ in the solution is from 0.01–0.12. More preferred is an $Al_2O_3/CrO_2$ ratio of 0.005–0.04, a $B_2O_3/SiO_2$ ratio of 0.12 and a $SiO_2/CrO_2$ ratio of 0.05–0.12. The foregoing ratios refer to weights of $Al_2O_3$, $B_2O_3$ and $SiO_2$ in solution and weight of $CrO_2$ particles to be coated. The quantity of silica deposited on the surface of the particle can be estimated by the procedure described below. The ratio of $SiO_2$ to $CrO_2$ is typically about 2 to 6% (weight/weight). Silica content greater than about 1% has been shown to be effective.

The amount of silica deposited on the surface of the surface reduced $CrO_2$ particles can be estimated using a plasma emission spectrometer to determine the total silicon content and thermal gravimetric analysis to determine the total weight of the particles. The silica shell is removed by heating an equal volume of the $CrO_2$ particles at about 50 C. for about 1 hour in 1M ammonium bifluoride. This suspension is then diluted with a 50 volumes of water and magnetically separated. The supernatant was analyzed for silicon content using Beckman Spectraspan ® IV DC plasma emission spectrometer (Beckman Instruments, Inc., Fullerton, CA) set to 251.61 nm. The thermal gravimetric analysis was performed using a Du Pont thermal gravimetric analyzer (E. I. du Pont de Nemours & Co., Inc., Wilmington, DE). As little as 0.5% silicon as a weight percent to chromium dioxide has been found to effectively protect the surface reduced $CrO_2$ magnetic particles. Typically, the weight of silicon ranges from 1–2% the weight of $CrO_2$. The % silicon can be converted to the % silica by multiplying by the ratio of the atomic weight of silicon to silica ($SiO_2$), approximately 2.14. The weight percent silica to $CrO_2$, is then typically from about 2–6%. However, use of higher ratios of $SiO_2$ to $CrO_2$ is possible.

The preferred particles including both the aluminate and $B_2O_3$ are manufactured as follows: One hundred grams of surface reduced $CrO_2$ particles suspended in 2.5 L water is heated to about 70°–90° C. with constant mechanical stirring. To this is added 5.0 mL of 40% to sodium aluminate ($NaAlO_2$) solution and the pH of the suspension adjusted to 9.0 with 2N sodium hydroxide. While stirring, 150 mL of a reagent containing 25 g of sodium metasilicate ($Na_2SiO_3$) and 6.25 g of sodium borate ($Na_2B_2O_4 \cdot 8H_2O$) is added dropwise over an hour period. The pH of the mixture is maintained at 9.0 by simultaneous dropwise addition of 5% sulfuric acid. The mixture is stirred for another 30 minutes at about 70°–90° C. to cure the particles. The pH is adjusted back to 7.0 with 5% sulfuric acid, cooled and the particles are dialized against water. The alumina content can also be determined in the same fashion as described for silica. The alumina content is typically about 0.5–3.0%. Alumina content greater than about 0.1% has been found effective. $B_2O_3$ in the silica layer is not required but is preferred. The weight ratio of $B_2O_3$ to $SiO_2$ is preferably 0.04–6%.

The effectiveness of the inorganic surface layer protective coating can be characterized by a long term chromate leaching test. The test is basically similar to the one described above except it is carried out at 37° C. for one week. Alternatively, an accelerated chromate leaching test, where the particles are first dried and heated to 25°, 80° and 140° C. for 90 minutes before being tested in the chromate leaching test, can be used.

The surface reduced, silica coated $CrO_2$ particles are coated with a silane, both to further stabilize the particle and to provide functional groups for covalent attachment of proteins, ligands, haptens or linker compounds directly or through coupling agents. The selection of silanes to bind antibodies to inorganic barriers is taught in Weetall, U.S. Pat. No. 3,652,761. A variety of useful silanes will be apparent to one skilled in preparing bioaffinity supports. Preferred silanes are 3-aminopropyltriethoxysilane, N-2-aminoethyl-3-aminopropyltriethoxysilane, diphenyldiethoxysilane, 1-trimethoxy-2-(m,p-chloromethyl)phenylethanesilane and n-dodecyltriethoxysilane. The most preferred is 3-aminopropyltriethoxysilane.

Silanization can be done in an aqueous or nonaqueous system but the preferred process is the aqueous phase silanization in which silane itself serves as a base catalyst. This works especially well with silanes containing amino functional groups such as 3-aminopropyltriethoxysilane. The reaction involves two steps that can occur in sequence or simultaneously. First is rapid hydrolysis of 3-aminopropyltriethoxysilane to the corresponding silanol and subsequent base catalyzed condensation to form a polymerized siloxane. The second is deposition of the silanol and polymerized siloxane onto the hydroxyl surface of the particles with subsequent covalent bond formation. One hundred grams of the surface reduced, silica coated particles suspended in 1.8 L water is dispersed wth an overhead mechanical stirrer and heated to 55° C. To this is added 200 mL of 3-aminopropyltriethoxysilane and the suspension is stirred mechanically for 12 to 18 hours at about 55° C. Maintaining adequate dispersion is critical at this stage to minimize the agglomerate size. Alternatively, ball mill or sand mill silanization is equally effective in producing the finely dispersed particles. The silanized particles are extensively washed with water at room temperature. The finished particles have a mean volume diameter of less than 10 μm as measured by the light scattering technique on a Microtrac ® [Particle Size Analyzer (Leeds & Northrup Instruments, North Wales, PA)], and a settling time of less than 20 minutes. The magnetic separation time in a 1000 gauss field with a one centimeter gap is less than 3 minutes. The particles are extensively washed to ensure removal of all adsorbed silane and stored as a 5% suspension in a 10 mM phosphate buffer, pH 7.4. The particles produce an absorbance value of <0.2 and preferably <0.05 in the chromate leaching test. The surface stabilized $CrO_2$ particles have been used as solid phase to develop highly sensitive and rapid immunoassays.

Surprisingly, it has been found that by appropriate surface treatment chromium dioxide magnetic particles can be made which are stable for long periods of time in aqueous solution. Further, these surface stabilized particles retain surprisingly excellent magnetic properties, allowing rapid separation in moderate strength magnetic fields. The ability to rapidly separate these particles from the reaction mixtures offers advantages in automating immunoassays. A still further unexpected result is the facility with which these ferromagnetic particles are redispersed after repeated exposure to a magnetic field, a property essential for use in automated immunoassay.

EXAMPLE 1

(A) Reductive Surface Treatment of $CrO_2$

Two hundred and fifty grams of upgraded heated chromium dioxide were mixed with one hundred grams of sodium bisulfite in 1750 mL of water. The mixture was milled in a W-250V-B Vertical Belt-Drive Colloid Mill (Greerco Corporation, Hudson, N.H.) for 45 min. and aged in a glass container for one week. The particles were dialyzed against distilled water to remove the excess sodium bisulfite. The chromate leaching test gave an absorbance=0.03, settling time=12 min.

(B) Silica Coating

One hundred grams of chromium dioxide particles from above were placed in a 3 liter beaker and 2.5 liters of distilled water were added. The particles were heated to 90° C.±2° C. with mechanical stirring. To the mixture was added 5.0 mL of sodium aluminate (40% solution) and the pH of the suspension was adjusted to 9 by the addition of 5% sulfuric acid. To this mixture was added 150 mL of water containing 25 grams of sodium metasilicate and 6.25 grams of sodium borate dropwise over a period of one hour. The pH of the mixture was maintained at 9±0.5 with the simultaneous dropwise addition of 5% sulfuric acid. Vigorous stirring was maintained throughout the reaction. After all the reagents were added, the mixture was heated at 90° C. and stirred for an additional 30 min. before the pH was adjusted to 7 with 5% sulfuric acid and allowed to cool to room temperature. The particles were dialyzed against distilled water. The chromate leaching test gave an absorbance=0.03, settling time=15 min. When aliquots were dried and heated at 25° C., 80° C., and 140° C. for 90 min. and then tested, the chromate leaching test gave absorbances=0.1, 0.2 and 0.25, respectively, compared to 0.33, 0.83 and 2.0 for the surfaced reduced particles.

(C) Silane Coating

One hundred grams of silica coated chromium dioxide particles were suspended in 1.8 liters of distilled water in a 2-liter round-bottom flask equipped with a mechanical stirrer, a reflux condensor and a temperature sensor. Two hundred mL of aminopropyltriethoxysilane was added and the mixture was stirred at 55° C. for 18 hours. The particles were washed three times with 13 liters of distilled water by settling and decantation. The washed particles were suspended in 10 mM phosphates buffer (pH 7) at 50 mg/mL. The chromate leaching test gave an absorbance=0.02, the settling time=8 min. When aliquots were dried and heated at 25° C. 80° C. and 140° C. for 90 min and tested, the chromate absorbances=0.05, 0.20 and 0.25, respectively.

(D) Digoxin Assay i. Preparation of Ouabain Coupling 5 g of ouabain-octahydrate were dissolved in 500 mL of hot distilled water and allowed to cool to room temperature. 7.3 g of sodium metaperiodate (NaI04) were added to the ouabain solution and stirred for two hours in the dark. The solution was passed through a bed of Dowex (I-X8) anion exchange resin (prepared by washing 250 g of the Dowex resin with water until the yellow color disappears). The oxidized ouabain solution was mixed with 500 mL of 1M sodium phosphate (pH 7.0) containing 10 g of BSA. The mixture was stirred for one hour and 0.64 g of sodium caynoborohydride ($NaCNBH_3$) added. The mixture was stirred at room temperature for 48-72 hours. The ouabain-BSA conjugate was dialyzed against running water for 12-24 hours and against 20 volumes of 0.015M sodium phosphate buffer (pH 7.0) at 4° C. for 16 hours. The conjugate was stored at 4° C.

ii. Protein Coupling

Ten mL of a 50 mg/mL suspension of the silane coated $CrO_2$ particles were washed three times with 50 mL of 10 mM phosphate buffer. To the washed particles 20 mL of 5% glutaraldehyde were added and mixed for 3 hours at room temperature. The activated particles were washed 5 times each with 50 mL of phosphate buffer and suspended in 10 mL of the same buffer. A solution of 40 mg of ouabain-BSA conjugate in 10 mL of buffer was added. The mixture was agitated at room temperature for 20 hours. The particles were washed once with 10 mM phosphate buffer and the unreacted aldehyde groups were quenched by the addition of 50 mL of 1M glycine (pH 8) and mixed for one hour. The protein particles were washed ten times with 50 mL each, of 10 mM phosphate±0.1% BSA+0.1% thimerosal, and stored in 50 mL of the same buffer at 4° C.

iii. Assay Procedure

To 50 μL of 0.15M sodium phosphate buffer (pH 7.8) was added 50 μL of Digoxin antibody-enzyme conjugate reagent (E. I. du Pont de Nemours & Co., Inc; Wilmington, DE) and 50 μL of human serum containing digoxin. The Digoxin Antibody-Enzyme conjugate reagent is a covalent conjugate of an F(ab')$_2$ antibody fragment from rabbit and anti-digoxin antisera and β-galactosidase. The mixture was incubated at 37° C. for 10 min and 50 μL of a 10 mg/mL ouabain-BSA-$CrO_2$ particles prepared above were added. Incubation was continued for 2 more minutes and the particles were separated on a magnetic separation unit (Corning Medical, Corning Glass Works, Medfield, MA). The supernatant was removed and the enzyme activity in 50 μL of the supernatant was measured on a Cobas-Bio® centrifugal analyzer (Roche Analytical Instrument, Inc., Nutley, NJ) using o-nitrophenylgalactoside as substrate. A series of human serum samples containing digoxin at concentrations from 0 to 5 ng/mL were tested as described. The background (B.G) and the 0 ng/mL to 5 ng/mL separation (Δ0,5) are were determined from those results and were 61 mA/min and 103 mA/min, respectively.

EXAMPLE 2

(A) Reductive Surface Treatment of $CrO_2$ 250 g of upgraded $CrO_2$ were mixed with 100 g of sodium bisulfite in 1750 mL of water. The mixture was milled in a W-250V-B Vertical Belt-Drive Colloid Mill (Greerce Corporation, Hudson, NH) for 45 minutes. The particles were washed with water and spray dried. 20 g of spray dried $CrO_2$ particles were washed twice with 200 mL of distilled water by decantation. The particles were dispersed in 200 mL of distilled water containing 20 grams of sodium bisulfite and 50 g of $\frac{1}{8}''$ glass beads in a 200 mL tissue culture flask. The mixture was rotated at 5 rpm for 48 hours at room temperature. The particles were separated from the glass beads and washed three times with 200 mL of 10 mM sodium phosphate buffer (pH 7) using magnetic separation. The chromate leaching test gave an absorbance = 0.03 and the settling time = 10 min.

(B) Silica Coating

Twenty grams of reductive surface treated $CrO_2$ prepared above were coated with silica as in Example 1(B).

(C) Silane Coating

Ten grams of silica coated chromium dioxide prepared as above were washed three times with 200 mL of acetone. Magnetic separation was used during the washes. The washed particles were dispersed in 450 mL of acetone in a 500 mL 3-neck round bottom flask equipped with a mechanical stirrer and a reflux condenser. Fifty mL of aminopropyltriethoxysilane were added and the mixture was refluxed with continuous stirring for 18 hours. The mixture was allowed to cool to room temperature. The particles were washed five times with 200 mL of acetone and dried at 140° C. for 90 min. The dried particles were milled with glass beads ($\frac{1}{8}''$) overnight in 10 mM phosphate buffer (pH 7) at 50 mg/mL concentration. The chromate leaching test gave an absorbance = 0.02 and the settling time = 3 min. When aliquots were dried and heated at 25° C., 80° C. and 140° C. for 90 min. then tested, the chromate leaching gave absorbances = 0.02, 0.02 and 0.02, respectivley.

EXAMPLES 3-8

Several surfaced reduced, silica coated $CrO_2$ samples were silane coated with a variety of silanes using a variety of solvents, coupled with ouabain-BSA and used in the digoxin assay as in Example 1. The results of this series of experiments are given in Table 1.

TABLE I

| EXAMPLE | SOLVENT | SILANE | CHROMATE LEACHING TEST A374 | SETTLING TIME MIN. | DIGOXIN ASSAY Δ 0,5 (B.G.) |
|---|---|---|---|---|---|
| 3 | Acetonitrile | 1 | 0.25 | 2.5 | 84(68) |
| 4 | Acetone | 2 | 0.04 | 5 | 72(71) |
| 5 | Acetone | 3 | 1.3 | 6 | 81(84) |
| 6 | Acetone | 4 | 0.25 | 2.5 | 70(92) |
| 7 | Acetone | 5 | 0.31 | 8 | |
| 8 | Acetone | 6 | 0.05 | 4 | 84(57) |

Silanes Used
1 3-aminopropyltriethoxysilane
2 N—2-aminoethyl-3-aminopropyltriethoxysilane
3 diphenyldiethoxysilane
4 1-trimethoxy-2-(m,p-chloromethyl)phenylethanesilane
5 n-dodecyltriethoxysilane
6 n-dodecyltriethoxysilane + ethylenediamine

EXAMPLE 9

Two-site Sandwich Immunoassay for Thyroid Stimulating Hormone (TSH)

A two-site sandwich immunoassay for TSH was developed using two distinct monoclonal antibodies, one specific to the α-subunit and the other specific to the β-subunit of TSH are used. The α specific antibody is used as a capture antibody and the β specific antibody as a detector antibody by conjugating it to the enzyme, alkaline phosphatase.

i. $CrO_2$ Particle Preparation

Surface reduction was done as described in Example 2A. Silica coating and silanization was done as described in Example 1B and C, respectively.

ii. Protein Coupling

Ten mL of a 5% slurry of silanized $CrO_2$ were washed 3 times with 50 mL each of 10 mM phosphate, pH 7.4. After the third wash, the particles are magnetically separated, the supernatant was aspirated, and to this wet cake 20 mL of 5% glutaraldehyde was added and rocked for 3 hours at room temperature. The glutaraldehyde activated particles were washed ten times with 50 mL each of coupling buffer (10 mM potassium phosphate, pH 7.4). After the last wash, the particles were resuspended in 10 mL buffer. To this was added 6 mg of purified α subunit specific antibody in 10 mL of coupling buffer and the mixture rocked for 20 hours at 4° C. The antibody coupled particles were washed once with coupling buffer, then the unreacted aldehyde groups were quenched by reaction with 50 mL of 1M glycine, pH 8.0 for 10 minutes. The particle reagent was washed extensively, 10 times with 50 mL each of the wash buffer (coupling buffer also containing 0.1% BSA), to remove all noncovalently bound antibodies. The final reagent was resuspended into 10 mL of the wash buffer containing 0.1% sodium azide as preservative, and stored at 4° C.

iii. Assay Procedure

The assay protocol was as follows: Fifty μL of serum sample or control serum was incubated with 10 μL of the antibody conjugate reagent from a Hybritech Tandem®-E TSH immunoenzymetric assay kit (Hybritech, Inc., San Diego, CA) at 37° C. for 10 minutes. To this was added 10 μL of the particle reagent and incubated for another 10 minutes. 500 μL of the wash solution consisting of 10 mM citrate buffer and 0.1% Triton X-100, pH 5.8, was added directly to the reaction mixture and the particles were magnetically separated on a magnetic separation unit (Corning Medical Corning Glass Works, Medfield, MA). The supernatant was aspirated and the cake washed with 500 μL of the wash solution. After the second wash, the wet cake was suspended in 100 μL of the substrate solution containing 10 mM PNPP (para-nitrophenyl phosphate) in 0.5M 2- amino-2-methyl-1-propanol (AMP), 2 mM $MgCl_2$, pH 10.3, incubated for 30 minutes at 37° C. The reaction was quenched with 200 μL of 50 mM EDTA, pH 10.4. A 125 μL aliquot was taken and the absorbance at 406 nm was determined in a Cobas-Bio ® centrifugal analyzer (Roche Analytical Instruments, Inc., Nutley, NJ).

iiii. Results

The following results were obtained with a series of human serum samples.

| TSH μIU/mL | Absorbance at 406 nm (Avg. of 3 readings) |
|---|---|
| 0 | 0.1135 |
| 5 | 0.1829 |
| 25 | 0.4830 |
| 50 | 0.7940 |

Other immunoassay configurations will be apparent to those skilled in the art. These samples are not meant to restrict the scope of this invention.

EXAMPLE 10

The coated $CrO_2$ particles with an α subunit specific anti-TSH monoclonal antibody attached as prepared in Example 9ii was used to deplete normal human serum of TSH.

1-mL of a 5% suspension of the TSH specific antibody particle was magnetically separated and the supernatant asperated. 10 mL of normal human serum was added and the mixture rocked overnight at 4° C. The particles were magnetically separated and the depleted serum collected. The response of the TSH depleted serum in the TSH assay described in Example 9 was essentially zero. When tested before depletion, the serum was found to contain 2.4 μIU/mL of TSH.

What is claimed is:

1. A magnetic particle useful as a solid support for bioaffinity separations or immunoassays comprising:
   a core of acicular rutile chromium dioxide having a specific surface area of 5–100 $m^2/g$,
   said chromium dioxide particle having a reduced surface characterized by a line in the X-ray diffraction pattern of the reduced chromium dioxide corresponding to an interplanar spacing of 316.8 pm;
   said core having an inorganic surface layer coating which resists oxygen diffusion;
   said inorganic surface layer coated core having an outer layer of a silane compound capable of binding proteins, ligands, haptens or linker compounds directly or through intermediate coupling agents to said inorganic surface layer coated core;
   said magnetic particle having a mean volume diameter of from 0.5 to 10 μm, and a remanent magnetization of less than 25 emu.

2. The particle of claim 1 wherein the inorganic surface layer is silica, the weight ratio of silica to $CrO_2$ being greater than about 1%.

3. The particle of claim 2 wherein the reduced core is coated with alumina, the weight ratio of alumina to $CrO_2$ being greater than about 0.1%.

4. A particle of claim 2 or 3 wherein said silica coating contains 0.04 to 6% $B_2O_3$ by weight.

5. A particle of claim 4 wherein the silane is selected from the group consisting of 3-aminopropyltriethoxysilane, N-2-aminoethyl-3-aminopropyltriethoxysilane, diphenyldiethoxysilane, 1-trimethoxy-2-(m,p-chloromethyl)phenylethanesilane, and n-dodecyltriethoxysilane.

6. A particle of claim 5 wherein the silane is 3-aminopropyltriethoxysilane.

7. A particle of claim 2 or 3 in which the weight ratio of $SiO_2$ to $CrO_2$ is 2 to 6% and the chromium dioxide core has a specific surface area of 30–80 $m^2/g$.

8. A particle of claim 2 or 3 in which the weight ratio of $SiO_2$ to $CrO_2$ is 2 to 6% and the chromium dioxide core has a specific surface area of 40–70 $m^2/g$.

9. A particle of claim 7 wherein said silica coating contains 0.04 to 6% $B_2O_3$ by weight.

10. A particle of claim 8 wherein said silica coating contains 0.04 to 6% $B_2O_3$ by weight.

11. A particle of claim 7 wherein the silane is selected from the group consisting of 3-aminopropyltriethoxysilane, N-2-aminoethyl-3-aminopropyltriethoxysilane, diphenyldiethoxysilane, 1-trimethoxy-2-(m,p-chloromethyl)phenylethanesilane, and n-dodecyltriethoxysilane.

12. A particle of claim 8 wherein the silane is selected from the group consisting of 3-aminopropyltriethoxysilane, N-2-aminoethyl-3-aminopropyltriethoxysilane, diphenyldiethoxysilane, 1-trimethoxy-2-(m,p-chloromethyl)phenylethanesilane, and n-dodecyltriethoxysilane.

13. A particle of claim 9 wherein the silane is selected from the group consisting of 3-aminopropyltriethoxysilane, N-2-aminoethyl-3-aminopropyltriethoxysilane, diphenyldiethoxysilane, 1-trimethoxy-2-(m,p-chloromethyl)phenylethanesilane, and n-dodecyltriethoxysilane.

14. A particle of claim 10 wherein the silane is selected from the group consisting of 3-aminopropyltriethoxysilane, N-2-aminoethyl-3-aminopropyltriethoxysilane, diphenyldiethoxysilane, 1-trimethoxy-2-(m,p-chloromethyl)phenylethanesilane, and n-dodecyltriethoxysilane.

15. A method of heterogeneous immunoassay wherein the particle of claims 1, 2 or 3 is used as a solid support.

16. A method of bioaffinity separation wherein the particle of claims 1, 2 or 3 is used as support material.

17. A method of claim 15 wherein said silica contains 0.04–6% $B_2O_3$ by weight, the weight ratio of $SiO_2$ to $CrO_2$ is 2–6% and the silane is selected from the group consisting of 3-amino-propyltriethoxysilane, N-2-aminoethyl-3-aminopropyl-triethoxysilane, diphenyldiethoxysilane, 1-trimethoxy-2-(m,p-chloromethyl)phenylethanesilane, and n-dodecyltriethoxysilane.

18. A method of bioaffinity separation wherein said silica contains 0.04–6% $B_2O_3$ by weight, the weight ratio of $SiO_2$ to $CrO_2$ is 2–6% and the silane is selected from the group consisting of 3-amino-propyltri-ethoxysilane, N-2-aminoethyl-3-aminopropyl-triethoxysilane, diphenyldiethoxysilane, 1-trimethoxy-2-(m,p-chloromethyl)phenylethanesilane, and n-dodecyl-triethoxysilane.

* * * * *